United States Patent [19]

Cahn

[11] Patent Number: 5,019,658
[45] Date of Patent: May 28, 1991

[54] SEPARATION OF PURE OPTICAL STEREOISOMERS BY PRESSURE CRYSTALLIZATION

[75] Inventor: Robert P. Cahn, Millburn, N.J.

[73] Assignee: Kobe Steel Limited, Kobe, Japan

[21] Appl. No.: 424,948

[22] Filed: Oct. 23, 1989

[51] Int. Cl.$^5$ .................. C07C 35/12; C07C 29/78
[52] U.S. Cl. ................... 568/829; 568/810; 568/831; 568/832; 568/833
[58] Field of Search ............ 568/810, 816, 821, 822, 568/829, 832, 838, 854, 856, 868, 875, 913, 833, 831

[56] References Cited

U.S. PATENT DOCUMENTS

| | | | |
|---|---|---|---|
| 3,053,880 | 9/1962 | Dale | 568/829 |
| 3,943,181 | 3/1976 | Fleisher et al. | 568/829 |
| 4,011,270 | 3/1977 | Carrington | 568/829 |
| 4,418,225 | 11/1983 | House | 568/829 |

FOREIGN PATENT DOCUMENTS 0055438 4/1983 Japan .................. 568/829

Primary Examiner—Werren B. Lone
Attorney, Agent, or Firm—Oblon, Spivak, McClelland, Maier & Neustadt

[57] ABSTRACT

The instant invention is an improvement in the method of producing optically pure sterioisomers from a racemic mixture. The method is based on the well-known fact that a supersaturated solution or melt of the racemic mixture can be seeded with just the crystals of the desired stereoisomer, which will then crystallize out selectively, leaving the undesired stereoisomer behind in the liquid mother liquor. The desired isomer, in crystaline form, can then be separated by simple liquid/solid separation from the undesired isomer remaining behind in the mother liquor. In the conventional method, supersaturation is achieved by careful cooling of a saturated solution or melt. In the present invention, supersaturation is achieved by increasing the ambient pressure over the saturated solution or melt of the racemic mixture, and relying on the fact that the melting temperature of a substance increases with increasing pressure, provided there is an increase in molar volume when the substance melts.

13 Claims, No Drawings

SEPARATION OF PURE OPTICAL STEREOISOMERS BY PRESSURE CRYSTALLIZATION

BACKGROUND OF THE INVENTION

Many optically active compounds are made from common, commercially available raw materials via organic syntheses which produce the racemic mixture of two optically active enantiomorphs, which then has to be separated by difficult procedures to recover the desired enantiomorph in pure form. This separation method is frequently one of the most complex parts of the synthesis operation, since the optical isomers have identical physical and chemical properties, except vis-a-vis other optical isomers.

A well-known technique for achieving this separation is to use supersaturation of the racemic mixture, either in the form of a melt, or of a solution in a solvent, and then crystallizing out only the desired enantiomorph by seeding the supersaturated system with crystals of the desired isomer. Supersaturation is achieved by preparing a saturated solution or melt of the racemic mixture, and then carefully subcooling this system to avoid spontaneous crystallization of both enantiomorphs. The degree of subcooling which can be achieved is obviously a function of the stability of the supersaturated system against spontaneous crystallization, of the presence of nucleating particles which could bring about spontaneous crystallization, and of the method of cooling the saturated solution. Wall or coil cooling introduces regions of low temperature where spontaneous crystallization can occur, and vigorous agitation can have the same undesirable effect. The degree of subcooling which can be reached is important in determining the yield of desirable isomer which can be achieved when the supersaturated system is seeded with crystals of that material. Obviously, a high degree of supercooling will result in a higher yield of desirable optical isomer per pass than only a small degree of subcooling.

Rather than lowering the temperature by withdrawing heat from a saturated system to enter the supersaturated domain, it is possible to bring this about by an adiabatic increase in the pressure on the system. This is due to the fact that the melting point of a substance increases with pressure, provided there is an increase in molar volume when the substance melts. Therefore, as the pressure of a saturated mixture, either a melt or a solution, is increased, the melting point of the constituents increases, and crystallization will occur. However, in many cases, this crystallization will be delayed, as the pressure is increased, resulting in a supersaturated system. Since the pressure on a system can be applied uniformly and gradually, without gradients and agitation, supersaturation is more likely and more extensive than in a thermal cycle. It will also permit using the selective seeding technique to systems which do not exhibit any or sufficient supercooling when the temperature is lowered.

BACKGROUND OF THE PRIOR ART

A typical separation of an optically active isomer using the supersaturation technique of the conventional process is described in U.S. Pat. No. 3,943,181. Here optically active l-menthol is produced from the racemic mixture by first converting the synthetic menthol (the racemic mixture) into an ester, followed by selective seeding of either the melt or one of several solutions of the racemic ester mixture to recover the desired ester isomer. Saponification of the ester yields the l-menthol product. Rather than working with the racemic mixture of l- and d-menthol directly, an ester has to be prepared first to capitalize on the principle of selective seeding of supersaturated solutions. The reason for this is that d,l-menthol does not form supersaturated solution or melts with a sufficient degree of supercooling to allow economic exploitation of the principle of selective seeding. This limitation introduces a cumbersome and potentially wasteful series of steps, esterification and saponification, into the overall synthesis procedure. Also, the degree of supercooling which can be utilized is limited to a few degrees C., severely proscribing the yield of desirable isomer per pass.

Conventional crystallization processes which are not based on solvent removal by evaporation utilize heat removal to lower the temperature of the melt or solution in order to crystallize out the desired product in relatively pure form. A recent development commercialized by the Kobe Steel Co. of Japan exploits the fact that the melting point of substances increases with pressure, provided there is an increase in molar volume of the substance when it undergoes melting. This process is described in a number of publications, such as M. Moritoki, "Crystallization and Sweating of p-Cresol by Application of High Pressure", Industrial Crystallization, 84, 373–376 (1984) and M. Moritoki, et al. "What is High Pressure Crystallization Process?", CEER (Chemical Economy & Engineering Review), December 1984, p. 30–35, published by the Chemical Economy Research Institute (Japan). Essentially, the mixture to be separated, either in the form of a melt, or as a solution in a suitable solvent, is introduced close to its melting temperature into a hydraulic press, where it is subjected to a timed pressure cycle. As the pressure is increased, up to about 1500–2000 kgf/cm$^2$, crystallization will occur. The cycle is continued by squeezing out the mother liquor while the pressure is gradually released, resulting in some additional purification as a result of "sweating", since the crystals formed will tend to melt as the pressure is reduced. The resultant crystal cake is then discharged from the press to complete the cycle. The overall cycle is of the order of 2 minutes. The process as described has been applied to the separation and purification of hydrocarbon isomers such as paraxylene, and to hydrocarbon derivatives like p-cresol. Supersaturation was observed in a number of the systems investigated, and seeding was practiced to enhance the yield and purity of the desired product. There is no mention of its use in the separation of optical isomers. The pressure crystallization process is also covered in Japanese Patent No. 57-35814

DESCRIPTION OF THE INVENTION

It has now been found that, surprisingly, the technique of crystallizing a saturated mixture, melt or solution, by subjecting it to elevated pressure can be advantageously applied to the separation of racemic mixtures and to the recovery and purification of optical isomers. This is based on the fact that when a saturated mixture is subjected to increasing pressure, supersaturation can occur which will delay the onset of crystallization beyond the pressure predicted by thermodynamic and phase equilibria. This supersaturation can be exploited by seeding the supersaturated system with crystals of the desired optical isomer to be recovered. Only the desired isomer will crystallize around the seed crystals introduced. The invention improves on the temperature induced selective crystallization technique by (1) allowing its use in systems not amenable to the temperature technique, but subject to supersaturation in the pressure system, (2) permitting higher degrees of supersaturation and resultant yields per pass than the temperature system. The reason for the latter is that pressure can be applied evenly to the whole system, while cooling a saturated solution or melt will inevitable introduce temperature gradients, i.e. spots of low temperature where incipient crystallization will occur. Also, stirring, another source of potential initiation of crystallization, is not necessary in the pressure system.

The technique is broadly applicable to the separation of racemic mixtures with melting points safely below the thermal decomposition temperature of the materials being handled. If the melting point is too high, a solvent can be introduced in sufficient amount to cause a melting point depression, so that the separation can proceed at a temperature low enough to be safely below the decomposition temperature. The solvent selected must be easily separable from the recovered isomer by conventional means such as distillation, extraction, flashing, washing with water, etc.

The resolution of the racemic mixture will proceed as follows in the present invention: The mixture to be separated is first melted, prior to its injection into the high pressure cylinder, and its temperature is adjusted as close to its atmospheric melting point as possible, say within $\pm 1°$ C., preferably to within less than $\pm 0.2°$ C. It may be advantageous to add to this mixture seed crystals of the enantiomorph (optical isomer) which it is desired to selectively crystallize out of the melt. Care must be taken to hold up this slurry only as shortly as possible in order to avoid melting the seed crystals. Therefore, the time between preparing the slurry and introducing the slurry into the high pressure cylinder should be kept very short, say less than 5 sec. Preferably, although not necessarily, the seed crystals are injected into the high pressure cylinder together with the feed melt.

After the melt slurry is injected into the high pressure cylinder, the pressure on the melt is increased to crystallization pressure over a time period of less than 1 minute, preferably less than 30 seconds. The crystallization pressure may be of the order of 100–2000 kgf/cm$^2$, but may be as high as 5000–10,000 kgf/cm$^2$. The pressure is maintained at the crystallization pressure for a period of 10 seconds to 2 minutes to allow equilibration and crystal growth. At the same time, the liquid discharge valve is opened to allow the mother liquor to be discharged. The pressure is then gradually reduced, which allows some melting of the crystals to take place which effectively washes the crystals and removes undesirables impurities as further liquid is expressed. This period of reducing pressure will last 30 seconds to 2 minutes. When the pressure has reached atmospheric, the cylinder is removed from the crystal mass of vice versa, which allows discharging the crystalline product from the apparatus, permitting a fresh charge of melt to be placed into the empty cylinder.

It may be advantageous to repeat the pressuring-depressuring steps a number of times to allow successive recrystallizations, increasing the product purity.

If the melting point of the racemic mixture to be separated is too high, a relatively small amount, of the order of 0.01 to 0.25 mol fraction, of a co-solvent can be added to the feed to depress the melting point. This co-solvent can be any material soluble in the feed racemic mixture, but easily separated from the product subsequently to the crystallization by water washing, distillation, extraction, drying, or can be left in the product without affecting its efficacy. The effect of this co-solvent is not only to lower the operating temperature in the crystallization step, but it may also extend the pressure range over which crystallization can be carried out and still recover only the desired optical isomer.

The pressure to which the system can be raised to bring about the selective crystallization of the desired optical isomer is obviously limited to be below the pressure at which spontaneous crystallization of the feed mixture will occurs in the absence of seed crystals. The higher this pressure, the greater the yield of desirable isomer in pure form per pass. The pressure is of the order of 100–500 kgf/cm$^2$ for pure melts, and may be as high as 5000 to 10000 kgf/cm$^2$ for systems containing co-solvents.

A typical system to which this process can be applied is the production of optically pure l-menthol, the common peppermint flavoring agent.

When it is made synthetically, the racemic l,d-menthol mixture is produced. This has to be separated, since only the l-isomer has the desired flavor. The residual d-isomer is recycled to an isomerization step, allowing eventual conversion of most of the menthol produced to the desirable l-form. d,l-Menthol has a melting point of 28°–38° C., so no co-solvent is required to allow operation at resonable temperatures. On the other hand, resolution of racemic mixtures of synthetic amino acids melt at too high a temperature, in excess of 200° C. for safe operation without co-solvent. In these cases, a co-solvent such as water or a low boiling organic acid may be advantageous.

It should be pointed out that the method of introducing the seed crystal into the supercooled mixture can be carried out in any number of ways, such as by direct injection into the mixture when it is being compressed, or other methods well known to anybody skilled in the art.

It is clear that the invention is not restricted to the recovery of optical isomers from racemic mixtures, but can be applied to any liquid mixture of optical isomers, provided it exhibits the property of effectively subcooling, i.e. remaining liquid when going from a condition above or at its melting point to a condition below its melting point. The invention is therefore applicable to mixtures of several compounds, where one or more of said compounds may be racemic mixtures of optical isomers, or such mixtures where one or more of said optical isomers may be in excess relative to its enantiomorph.

As a specific example, the instant invention is not only applicable to the separation of a racemic mixture, i.e. a 50/50 mixture of optical isomers, but also to a 60/40 mixture of the l- and d- siomers, and to the recovery of, say, the l-menthol isomer from a 45/55 mixture of l- and d-menthol, and from a mixture of said 45/55 menthol-mixture together with racemic mixtures of neomenthol and neoisomenthol.

Having thus described the present invention, what is claimed is:

1. A process for separating an optical isomer from a mixed isomer feed, comprising melting the racemic mixture at a temperature below its thermal decomposition temperature, adjusting the temperature of the melted mixture to a temperature close to its atmospheric pressure melting point, subjecting the mixture to increasing pressure, resulting in an increase in the melting point of the mixture, maintaining said pressure below the point where spontaneous crystallization of the mixture would occur, seeding said mixture with crystals of the desired optical isomer, and recovering the crystals of the desired optical isomer from the mother liquor by liquid/solid separation.

2. A process of claim 1, where said mixture is selected from the group comprising a mixture of optical isomers, a racemic mixture, a mixture of optical isomers and a co-solvent, and a racemic mixture and co-solvent.

3. A process of claim 1, where said temperature close to the melting is within ±1° C. of said atmospheric pressure melting point.

4. A process of claim 1, where said temperature close to the melting is within ±0.2° C. of said atmospheric pressure melting point.

5. A process of claim 1, where said elevated pressure is below 5000 kgf/cm$^2$.

6. A process of claim 1, where said mixed isomer feed comprises l- and d-menthol, and where the desired optical isomer is l-menthol.

7. A process for separating a desired optical isomer from a mixture of optical isomers which comprising the following steps:
(a) melting said mixture and maintaining the melt within ±1° C. of the melting point
(b) adding crystals of the desired optical isomer to be separated to said melt and injecting the resultant slurry into a cylinder
(c) carrying out selective crystallization of the desired isomer by raising the pressure in said cylinder over a period not exceeding 1 minute to a pressure below the pressure where spontaneous crystallization would occur,
(d) withdrawing residual liquid from said cylinder while the pressure is maintained above atmospheric
(e) gradually reducing the pressure in the cylinder, while continuing to remove liquid from the cylinder
(f) removing the crystals of desired optical isomer from the cylinder when the pressure has reached atmospheric.

8. A process according to claim 7, in which said desired optical isomer is l-menthol.

9. A process according to claim 8, wherein said mixture comprises l,d-menthol

10. A process according to claim 1 where said mixture is a mixture of the two enantiomorphs of an optically active compound 11. A process according to claim 1, where said mixture comprises the two enantiomorphs of an optically active compound, and a co-solvent 12. A process according to claim 1, where said mixture comprises (a) the two enantiomorphs of an optically active compound, one of which is the said desired optically active compound, and (b) other racemic mixtures 13. A process according to claim 12, where said two enantiomorphs are l- and d-menthol, and where said other racemic mixtures are selected from the group of l,d-neomenthol, l,d-isomenthol and l,d-neoisomenthol

* * * * *